United States Patent [19]
Han

[11] Patent Number: 5,888,740
[45] Date of Patent: Mar. 30, 1999

[54] DETECTION OF ANEUPLOIDY AND GENE DELETION BY PCR-BASED GENE- DOSE CO-AMPLIFICATION OF CHROMOSOME SPECIFIC SEQUENCES WITH SYNTHETIC SEQUENCES WITH SYNTHETIC INTERNAL CONTROLS

[75] Inventor: Jian Han, Birmingham, Ala.

[73] Assignee: Genaco Biomedical Products, Inc., Birmingham, Ala.

[21] Appl. No.: 933,641

[22] Filed: Sep. 19, 1997

[51] Int. Cl.⁶ .............................. C12Q 1/68; C12P 19/34
[52] U.S. Cl. ................................. 435/6; 435/91.2
[58] Field of Search ....................... 435/6, 91.2; 536/23.1

[56] References Cited

U.S. PATENT DOCUMENTS

| | | | |
|---|---|---|---|
| 4,818,708 | 4/1989 | Kerkay | 436/516 |
| 4,940,659 | 7/1990 | Warrington et al. | 435/7 |
| 4,983,044 | 1/1991 | Schweber | 356/443 |
| 5,213,961 | 5/1993 | Bunn et al. | 435/6 |
| 5,252,489 | 10/1993 | Macri | 436/87 |
| 5,258,907 | 11/1993 | Macri | 364/413.01 |
| 5,324,667 | 6/1994 | Macri | 435/518 |
| 5,324,668 | 6/1994 | Macri | 435/6 |
| 5,447,841 | 9/1995 | Gray et al. | 435/6 |
| 5,476,774 | 12/1995 | Wang et al. | 435/6 |
| 5,506,150 | 4/1996 | Canick et al. | 436/510 |
| 5,605,843 | 2/1997 | Canick et al. | 436/510 |
| 5,612,473 | 3/1997 | Wu et al. | |

FOREIGN PATENT DOCUMENTS

| | | |
|---|---|---|
| WO 9008325 | 7/1990 | WIPO . |
| WO 9321342 | 6/1993 | WIPO . |
| WO 9403638 | 2/1994 | WIPO . |

OTHER PUBLICATIONS

Miller, D., et al., Lancet, Semi–Quantitative Detection of Down's Syndrome with PCR, Sep. 5, 1992, vol. 340 pp. 620–621.

Zheng, Y L, et al., Prenat. Diagn., Analysis of Chromosome 21 Copy Number in Uncultured Amniocytes by Fluorescence in Sita Hybridization Using a Cosmid Contiz., Nov., 1992, 12(11) pp. 931–943.

Peterson, M B, et al., Am J. Hum. Genet., Comparative Study of Microsatellite and Cytogenetic Markers for Detecting the Origin of the Nondisjoined Chromosome 21 in Down Syndrome, Sep., 1992, 51(3) pp. 516–525.

Celi, Francesco, S., Genomics, Determination of Gene Dosage by Quantitative Adaptation of the Polymeoase Chain Reaction (gd–PCR): Rapid Detection of Deletions and Duplications of Gene Sequences, (1994),21 pp. 304–310.

McCormick, Mary Kay, Genomics, Molecular Genetic Approach to the Characterization of the "Down Syndrome Region" of Chromosome 21, (1989),pp. 325–331.

Petersen, Michael B., Am. J. Human. Genet., Use of Short Sequence Repeat DNA Polymorphisms after PCR Amplification to Detect Origin of the Additional Chromosome 21 in Down's Syndrome, (1991), 48 pp. 65–71.

Eggeling, Ferdinand von, Hum. Genet., Rapid Detection of Tresomy 21 by Quantitative PCR, (1993), 91 pp. 567–570.

Pangalos, C., Am. J. Human Genet., Understanding the Mechanism(s) of Mosaic Tresomy 21 by using DNA Polymorphism Analysis, (1994), 54 pp. 473–481.

Pertl, B., Rapid Detection of Trisomies 21 and 18 and Sexing by Quantative Fluorescent Multiplex PCR Hum. Genet. (1996) 98: 55–59.

Lee, Hsien–Hsiung, Human. Genet., Rapid Detection of Trisomy 21 by Homologous Gene Quantitative PCR (HGQ–PCR), (1997), 99 pp.364–367.

Mansfield, E.S., Hum. Mol. Genet., Diagnosis of Down's Syndrome and other Aneuploidies using Quantitative PCR and Small Tandem Repeat Polymorphisms, (1993), 2 (1) pp. 43–50.

Brown et al., Am. J. Med. Genet. 63(2): 373–377. 1996.

Celi et al., Genomics 21:304–310, 1994.

Leu, Science 237:1570. 1987.

*Primary Examiner*—Eggerton A. Campbell
*Attorney, Agent, or Firm*—Lyon & Lyon, LLP

[57] ABSTRACT

Disclosed is a method and composition of matter for PCR-based gene dosage analysis. The invention provides internal control DNA sequences that are the same length and same G-C content. The method does not require sized separation of the amplified products. Instead, the method utilizes hybridization and ELISA like colormetric screening. The invention further provides for tightly controlled internal standards for comparing gene dosage by placing one copy of various chromosome markers on one plasmid.

24 Claims, 8 Drawing Sheets

| Phenotype | Chromosome loci 21 18 13 X | Expected Ratio |
|---|---|---|
| Normal Female: | $\frac{a}{b} : \frac{c}{d} : \frac{e}{f} : \frac{g}{h}$ | = 1:1:1:1 |
| Normal Male: | $\frac{a}{b} : \frac{c}{d} : \frac{e}{f} : \frac{g}{h}$ | = 1:1:1:0.5 |
| Female Trisomy 21: | $\frac{a}{b} : \frac{c}{d} : \frac{e}{f} : \frac{g}{h}$ | = 1.5:1:1:1 |
| Male Trisomy 21: | $\frac{a}{b} : \frac{c}{d} : \frac{e}{f} : \frac{g}{h}$ | = 1.5:1:1:0.5 |
| Female Trisomy 18: | $\frac{a}{b} : \frac{c}{d} : \frac{e}{f} : \frac{g}{h}$ | = 1:1.5:1:1 |
| Male Trisomy 18: | $\frac{a}{b} : \frac{c}{d} : \frac{e}{f} : \frac{g}{h}$ | = 1:1.5:1:0.5 |
| Female Trisomy 13: | $\frac{a}{b} : \frac{c}{d} : \frac{e}{f} : \frac{g}{h}$ | = 1:1:1.5:1 |
| Male Trisomy 13: | $\frac{a}{b} : \frac{c}{d} : \frac{e}{f} : \frac{g}{h}$ | = 1:1:1.5:0.5 |
| Turner's (X0): | $\frac{a}{b} : \frac{c}{d} : \frac{e}{f} : \frac{g}{h}$ | = 1:1:1:0.5 |
| Kleinfelter's (XXY): | $\frac{a}{b} : \frac{c}{d} : \frac{e}{f} : \frac{g}{h}$ | = 1:1:1:1 |
| Triple X syndrome: | $\frac{a}{b} : \frac{c}{d} : \frac{e}{f} : \frac{g}{h}$ | = 1:1:1:1.5 |

Figure 5

SEQUENCE LISTING ( 1 ) GENERAL INFORMATION:

( i i i ) NUMBER OF SEQUENCES: 32

( 2 ) INFORMATION FOR SEQ ID NO:1:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: N ( i v ) ANTI-SENSE: N ( x i ) SEQUENCE DESCRIPTION: SEQ ID NO:1:

GGGAATTCAC ATGGATGCAC CAGAGACAGA AC    32

( 2 ) INFORMATION FOR SEQ ID NO:2:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE:DNA ( i i i ) HYPOTHETICAL: N ( i v ) ANTI-SENSE: Y ( x i ) SEQUENCE DESCRIPTION: SEQ ID NO:2:

GGGAATTCGC TATGCGTGTG TGGATTGTGT GT    32

( 2 ) INFORMATION FOR SEQ ID NO:3:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE:oligomer ( i i ) MOLECULE TYPE:DNA ( i i i ) HYPOTHETICAL: N ( i v ) ANTI-SENSE: N ( x i ) SEQUENCE DESCRIPTION: SEQ ID NO:3:

GAACCGTGAC AGGCTACCCC CTCCTA    26

( 2 ) INFORMATION FOR SEQ ID NO:4:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE:DNA ( i i i ) HYPOTHETICAL: N ( i v ) ANTI-SENSE: Y ( x i ) SEQUENCE DESCRIPTION: SEQ ID NO:4:

CTGTCACGGT    TCACAACCCA    GCCTTC                                             2 6

( 2 ) INFORMATION FOR SEQ ID NO:5:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE:DNA ( i i i ) HYPOTHETICAL: N ( i v ) ANTI-SENSE: N ( x i ) SEQUENCE DESCRIPTION: SEQ ID NO:5:

GGGAATTCCA    AGAAGACAGT    GCAGCCACCT                                         3 0

( 2 ) INFORMATION FOR SEQ ID NO:6:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE:DNA ( i i i ) HYPOTHETICAL: N ( i v ) ANTI-SENSE: Y ( x i ) SEQUENCE DESCRIPTION: SEQ ID NO:6:

GGGAATTCCC    AAAGAAGCGC    CCGATGGA                                           2 8

( 2 ) INFORMATION FOR SEQ ID NO:7:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE:DNA ( i i i ) HYPOTHETICAL: N ( i v ) ANTI-SENSE: N ( x i ) SEQUENCE DESCRIPTION: SEQ ID NO:7:

AGCCACCGAC    AGGATATGCC    AGGCAT                                             2 6

( 2 ) INFORMATION FOR SEQ ID NO:8:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE:DNA ( i i i ) HYPOTHETICAL: N ( i v ) ANTI-SENSE: Y ( x i ) SEQUENCE DESCRIPTION: SEQ ID NO:8:

CTGTCGGTGG    CTGATTGGCC    AGGTAC                                             2 6

(2) INFORMATION FOR SEQ ID NO:9:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE:DNA (iii) HYPOTHETICAL: N (iv) ANTI-SENSE: N (xi) SEQUENCE DESCRIPTION: SEQ ID NO:9:

GGGAATTCGT GTCCTGTCTT CCTTCCTCTG C     31

(2) INFORMATION FOR SEQ ID NO:10:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE:DNA (iii) HYPOTHETICAL: N (iv) ANTI-SENSE: Y (xi) SEQUENCE DESCRIPTION: SEQ ID NO:10:

GGGAATTCGC GTCATTATCT CTGCGGTTTG     30

(2) INFORMATION FOR SEQ ID NO:11:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE:DNA (iii) HYPOTHETICAL: N (iv) ANTI-SENSE: N (xi) SEQUENCE DESCRIPTION: SEQ ID NO:11:

GGCTCCGGTG CTGGTTTGCG GCCTGT     26

(2) INFORMATION FOR SEQ ID NO:12:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE:DNA (iii) HYPOTHETICAL: N (iv) ANTI-SENSE: Y (xi) SEQUENCE DESCRIPTION: SEQ ID NO:12:

AGCACCGGAG CCAAGAGGGC GCGTCC     26

(2) INFORMATION FOR SEQ ID NO:13:

( i ) SEQUENCE CHARACTERISTICS:
   ( A ) LENGTH: 32 base pairs
   ( B ) TYPE: nucleic acid
   ( C ) STRANDEDNESS: single
   ( D ) TOPOLOGY: linear ( i i ) MOLECULE TYPE:DNA ( i i i ) HYPOTHETICAL: N ( i v ) ANTI-SENSE: N ( x i ) SEQUENCE DESCRIPTION: SEQ ID NO:13:

GGGAATTCGC TCTAGGTGAA CATGGAGAAT GG  32

( 2 ) INFORMATION FOR SEQ ID NO:14:

( i ) SEQUENCE CHARACTERISTICS:
      ( A ) LENGTH: 32 base pairs
      ( B ) TYPE: nucleic acid
      ( C ) STRANDEDNESS: single
      ( D ) TOPOLOGY: linear ( i i ) MOLECULE TYPE:DNA ( i i i ) HYPOTHETICAL: N ( i v ) ANTI-SENSE: Y ( x i ) SEQUENCE DESCRIPTION: SEQ ID NO:14:

GGGAATTCTC AACTGTGAGG CGGAATCAAA AG  32

( 2 ) INFORMATION FOR SEQ ID NO:15:

( i ) SEQUENCE CHARACTERISTICS:
      ( A ) LENGTH: 26 base pairs
      ( B ) TYPE: nucleic acid
      ( C ) STRANDEDNESS: single
      ( D ) TOPOLOGY: linear ( i i ) MOLECULE TYPE:DNA ( i i i ) HYPOTHETICAL: N ( i v ) ANTI-SENSE: N ( x i ) SEQUENCE DESCRIPTION: SEQ ID NO:15:

CAGGGTTGCA CAGGTTGCTT CACTTC  26

( 2 ) INFORMATION FOR SEQ ID NO:16:

( i ) SEQUENCE CHARACTERISTICS:
      ( A ) LENGTH: 26 base pairs
      ( B ) TYPE: nucleic acid
      ( C ) STRANDEDNESS: single
      ( D ) TOPOLOGY: linear ( i i ) MOLECULE TYPE:DNA ( i i i ) HYPOTHETICAL: N ( i v ) ANTI-SENSE: Y ( x i ) SEQUENCE DESCRIPTION: SEQ ID NO:16:

TGTGCAACCC TGGAATATAT CAGGGG  26

( 2 ) INFORMATION FOR SEQ ID NO:17:

( i ) SEQUENCE CHARACTERISTICS:
      ( A ) LENGTH: 29 base pairs
      ( B ) TYPE: nucleic acid
      ( C ) STRANDEDNESS: single (D) TOPOLOGY: linear (ii) MOLECULE TYPE:DNA (iii) HYPOTHETICAL: N (iv) ANTI-SENSE: N (xi) SEQUENCE DESCRIPTION: SEQ ID NO:17:

AAATATTAAT CTCAGTCCTA GTGGGAGAA 29

(2) INFORMATION FOR SEQ ID NO:18:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE:DNA (iii) HYPOTHETICAL: N (iv) ANTI-SENSE: N (xi) SEQUENCE DESCRIPTION: SEQ ID NO:18:

AAATATTAAT TGTGAACCGT GACAGGCTA 29

(2) INFORMATION FOR SEQ ID NO:19:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE:DNA (iii) HYPOTHETICAL: N (iv) ANTI-SENSE: N (xi) SEQUENCE DESCRIPTION: SEQ ID NO:19:

AAATATTAAA CAGCAAGTAC CATGGACCA 29

(2) INFORMATION FOR SEQ ID NO:20:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE:DNA (iii) HYPOTHETICAL: N (iv) ANTI-SENSE: N (xi) SEQUENCE DESCRIPTION: SEQ ID NO:20:

AAATATTAAA ATCAGCCACC GACAGGATA 29

(2) INFORMATION FOR SEQ ID NO:21:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE:DNA (iii) HYPOTHETICAL: N (iv) ANTI-SENSE: N (xi) SEQUENCE DESCRIPTION: SEQ ID NO:21:

AAATATTAAT GGTTGCGCTG GTTCTTGCC 29

(2) INFORMATION FOR SEQ ID NO:22:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE:DNA (iii) HYPOTHETICAL: N (iv) ANTI-SENSE: N (xi) SEQUENCE DESCRIPTION: SEQ ID NO:22:

AAATTATTAA TCTTGGCTCC GGTGCTGGTT 30

(2) INFORMATION FOR SEQ ID NO:23:

(i) SEQUENCE CHARACTERISTICS:
(A) LENGTH: 29 base pairs
(B) TYPE: nucleic acid
(C) STRANDEDNESS: single
(D) TOPOLOGY: linear (ii) MOLECULE TYPE:DNA (iii) HYPOTHETICAL: N (iv) ANTI-SENSE: N (xi) SEQUENCE DESCRIPTION: SEQ ID NO:23:

AAATATTAAT CTATGTTCCT GGAAGGACG 29

(2) INFORMATION FOR SEQ ID NO:24:

(i) SEQUENCE CHARACTERISTICS:
(A) LENGTH: 29 base pairs
(B) TYPE: nucleic acid
(C) STRANDEDNESS: single
(D) TOPOLOGY: linear (ii) MOLECULE TYPE:DNA (iii) HYPOTHETICAL: N (iv) ANTI-SENSE: N (xi) SEQUENCE DESCRIPTION: SEQ ID NO:24:

AAATATTAAA TTCCAGGGTT GCACAGGTT 29

(2) INFORMATION FOR SEQ ID NO:25:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE:DNA (genomic)

(iii) HYPOTHETICAL: N (iv) ANTI-SENSE: N ( x i ) SEQUENCE DESCRIPTION: SEQ ID NO:25:

ACATGGATGC ACCAGAGACA GAAC 24

( 2 ) INFORMATION FOR SEQ ID NO:26:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE:DNA (genomic)

( i i i ) HYPOTHETICAL: N ( i v ) ANTI-SENSE: Y ( x i ) SEQUENCE DESCRIPTION: SEQ ID NO:26:

GCTATGCGTG TGTGGATTGT GTGT 24

( 2 ) INFORMATION FOR SEQ ID NO:27:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE:DNA (genomic)

( i i i ) HYPOTHETICAL: N ( i v ) ANTI-SENSE: N ( x i ) SEQUENCE DESCRIPTION: SEQ ID NO:27:

CAAGAAGACA GTGCAGCCAC CT 22

( 2 ) INFORMATION FOR SEQ ID NO:28:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE:DNA (genomic)

( i i i ) HYPOTHETICAL: N ( i v ) ANTI-SENSE: Y ( x i ) SEQUENCE DESCRIPTION: SEQ ID NO:28:

CCAAAGAAGC GCCCGATGGA 20

( 2 ) INFORMATION FOR SEQ ID NO:29:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE:DNA (genomic)

( i i i ) HYPOTHETICAL: N ( i v ) ANTI-SENSE: N ( x i ) SEQUENCE DESCRIPTION: SEQ ID NO:29:

GTGTCCTGTC TTCCTTCCTC TGC 23

( 2 ) INFORMATION FOR SEQ ID NO:30:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE:DNA (genomic)

( i i i ) HYPOTHETICAL: N ( i v ) ANTI-SENSE: Y ( x i ) SEQUENCE DESCRIPTION: SEQ ID NO:30:

GCGTCATTAT    CTCTGCGGTT    TG                                                2 2

( 2 ) INFORMATION FOR SEQ ID NO:31:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE:DNA (genomic)

( i i i ) HYPOTHETICAL: N ( i v ) ANTI-SENSE: N ( x i ) SEQUENCE DESCRIPTION: SEQ ID NO:31:

GCTCTAGGTG    AACATGGAGA    ATGG                                              2 4

( 2 ) INFORMATION FOR SEQ ID NO:32:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: N ( i v ) ANTI-SENSE: Y ( x i ) SEQUENCE DESCRIPTION: SEQ ID NO:32:

TCAACTGTGA    GGCGGAATCA    AAAG                                              2 4

DETECTION OF ANEUPLOIDY AND GENE DELETION BY PCR-BASED GENE- DOSE CO-AMPLIFICATION OF CHROMOSOME SPECIFIC SEQUENCES WITH SYNTHETIC SEQUENCES WITH SYNTHETIC INTERNAL CONTROLS

FIELD OF THE INVENTION

The present invention relates to a method for prenatal detection of fetal chromosome aneuploidy, including trisomy 21(Down's syndrome), trisomy 13, trisomy 18, and sex chromosome abnormalities as well as detection of microsome deletion syndromes, including Prader-Willi and Angelman syndrome, William syndrome, Smith-Magenis syndrome, DiGeorge syndrome, Miller-Dieker syndrome and other like disorders. More particularly, the present invention relates to a new method of detecting aneuploidy and microsome deletion using synthetic internal controls that provide advanced accuracy in determining chromosome copy number and chromosome deletion mutations by strictly controlling the quantity of the internal control sequences and relative rates of polymerase chain reaction (PCR) for test versus control DNA sequences.

BACKGROUND OF THE INVENTION

One form of common chromosome mutation is aneuploidy wherein the number of individual chromosomes present in a cell either increases or decreases from that present in a normal cell. The absence of one chromosome from the diploid complement is called "monosomy". The presence of an extra chromosome is called "trisomy". Trisomy 21 is a condition wherein there exists an extra chromosome 21. This trisomy is the most common form of aneuploidy and gives rise to Down's syndrome which is the congenital manifestation of severe mental retardation.

Generally, the diagnosis of Down's syndrome and other aneuploidies requires obtaining fetal cells by amniocentesis or chorionic villus sampling. This requires routine cytogenetic procedures which include the necessity of cell culture (up to 7–14 days), chromosome preparation and karyotyping. This process is lengthy, expensive and labor intensive. Recently, a molecular cytogenetic technique for detecting aneuploidy, namely, fluorescent in situ hybridization (FISH) has been developed. Although FISH is relatively fast and accurate, performance of the FISH method requires highly trained technicians and expensive equipment and reagents. In U.S. Pat. No. 5,213,961 by Bunn et al., is disclosed a method of quantitative PCR by competitive methodology. In that invention, the parameters affecting DNA amplification and a mechanism to distinguish differences in template (both test and control) ratios and copy numbers are discussed. The Bunn disclosure addressed as a primary object of the invention such parameters and their effect on the amplification process. These parameters were believed to arise predominantly from the nature of the DNA primers and their respective primer binding sites. The invention disclosed that it is necessary for such primers and binding sites of the control and test DNA sequences to be functional equivalents of one another. Emphasis was placed on the fact that PCR amplification was initiated utilizing identical primers for the control and test sequences. Moreover, that invention discussed the capacity to distinguish the test sequence from the control sequence by changing the size of the control sequence (by either deletion or insertion) as much as 100 to 200 base pairs. The Bunn invention also discussed altering the control sequence such as by substitution of sequence by site specific mutagenesis either creating or destroying an restriction enzyme cleavage site. It was reasoned that if the primers and binding sites were functional equivalents, then the amplification process could progress equivalently at similar rates (even if the control sequence was longer or shorter than the test sequence).

The invention disclosed in the Bunn patent further assumed that the described method would not be dependent upon variables which normally affect PCR amplification and that such method would therefore allow quantitation between template species (i.e. control and test sequence) regardless of such usual variables as long as the reaction would give good amplification of template DNA. However, the Bunn invention overlooked critical elements in the relative amplification rates that are inherently introduced by altering control and test sequence primer site lengths, control template sequence lengths, and guanine (G) and cytosine (C) content of such sequences. Moreover, the detection methodology of that invention disclosed and discussed only such means as are compatible with identification of DNA species via ethydium bromide, radioactivity, or colorimetric technology in conjunction with gel electrophoresis techniques and the like. Thus, the reasoning contemplated for introducing point mutations in the control sequence was based solely on a desire to create restriction enzyme sites as a means by which amplified DNA segments could be distinguishable from one another based solely on size.

In another invention, PCT application WO 94/03638 by Mansfield, a method is disclosed whereby aneuploidy may be detected by utilization of short tandem repeat DNA sequences present in chromosome DNA. In that invention, PCR methodology was utilized to amplify the short tandem repeat sequences. There are, however, two limitations for this method. One drawback is that not all Down's patients are heterozygous at the polymorphic site. About 25% of Down's patients are caused by a meiosis II nondisjunction error wherein two of the three chromosome 21s present in the cells are genetically identical. Therefore, the homozygosity resulting from this error will render a significant portion of the affected patient population unidentifiable by the proposed method. The second limitation of the disclosed method is that it differentiates alleles based on the size of the polymorphic PCR products. The problem here, as described above, is that the detection method must be capable of distinguishing size differences and also that because smaller fragments amplify more readily, errors can arise when calculating ratios. In some instances, larger species may be over shadowed by the amplification of the smaller species. This is possible even where the same PCR primers are used to amplify DNA sequence from the same or from different alleles.

In yet another example, determination of gene-dosage by PCR was disclosed (Genomics 21, 304–310, 1994 Francesco, C. et al.) wherein internal control DNA sequence was designed as a deletion mutant of the wildtype sequence. Again, quantitative analysis was dependant upon gel electrophoresis and measuring radioactivity of the different sized products.

Each of the above examples fail to consider the significant effect of amplification rate differences that even a small change in molecule size or G and C content in DNA bases have on the ultimate quantity of DNA segments resulting from a plurality of PCR thermocycles. Moreover, each of the above methodologies requires detection of the amplified species by first electrophoresing the amplified DNA to separate the amplified species. Thus, there is still a need in the art of quantitative PCR as such technology relates to the detection of aneuploidy, and other chromosomal anomalies, for a methodology which can accurately determine gene copy number without the occurrence of unreliable results derived from factors that inherently affect amplification of which template length, G and C content and ultimate detection methodology are primary components.

SUMMARY OF THE INVENTION

The current invention is directed to composition of matter and method for fast, accurate, and inexpensive detection of chromosome aneuploidy, including trisomy 21, trisomies 13 and 18, and sex chromosome abnormalities. The current invention is also directed to composition of matter and methods for detection of chromosomal abnormalities such as microchromosome deletion syndromes including Prader-Willi and Angelman syndrome, William syndrome, Smith-Magenis syndrome, DiGeorge syndrome, Miller-Dieker syndrome and other like disorders. Additionally, the current invention is directed to compositions of matter and methods of detecting cancer related gene dosage alterations, such as loss of heterozygosity (LOH).

One preferred embodiment of the invention relates to DNA templates engineered for use as internal controls during PCR reactions for quantitative measurement of gene dosage. These DNA templates are designed so that amplification will occur at the same rate for the control templates as the "test" sample DNA templates. Moreover, these templates are detectable at equivalent efficiencies in an ELISA-like assay providing enhanced accuracy in quantitatively determining chromosome copy number.

A key feature of the internal control templates of the present invention is that they have the identical length as that of the test DNA templates. Moreover, another preferred embodiment of the invention is that the internal control templates also have the same G and C content as the test templates.

Another object of the present invention is to provide a method and materials which may be used for prenatal detection of Down's syndrome and other aneuploidies and chromosome disorders by quantitative PCR.

Another object of the present invention is to provide a method and materials for prenatal detection of Down's syndrome and other aneuploidies and chromosome disorders by quantitative PCR using specially engineered DNA templates as internal controls. A preferred embodiment of the invention contemplates designing control templates such that an internal section of the control DNA sequence comprises the same nucleotide base pair content (i.e. G,C,A, and T) as the wildtype test sequence but such internal section having a DNA sequence that is either randomized or specifically arranged such that the resulting DNA sequence (the "mutant" section) is not homologous to the natural wildtype test sequence.

Yet another object of the present invention is to provide a method and materials for prenatal detection of Down's syndrome and other aneuploidies and chromosome disorders by comparing the quantity of chromosome specific PCR products amplified from the test samples and the internal controls in the same PCR reaction tube.

A further object of the present invention is to provide a method and materials for prenatal detection of Down's syndrome and other aneuploidies and chromosome disorders by comparing the quantity of chromosome specific PCR products amplified from wildtype and internal control DNAs using ELISA format in microplate well arrays. A preferred embodiment of the invention contemplates attaching DNA sequences to ELISA microplates wherein the DNA in any one particular microplate includes sequence homologous to either wildtype template or an internal control DNA's internal mutant section. These microwell attached sequences make up capture sequences that will hybridize to amplified test and control sequence (the capture sequence). Yet another embodiment of the invention contemplates designing the annealing characteristics of the wildtype and its capture sequence and the internal control mutant section and its capture sequence so that hybridization and washing conditions can be normalized for all tests conducted on the same microtiter plate. In other words, the melt temperature and stringency of washing conditions are the same.

Yet a further object of the present invention contemplates incorporating one copy of each of several different internal control DNA sequences on a single plasmid. Each such internal control is designed to a different chromosome aneuploidy or chromosome disorder. The preferred embodiment of this feature of the invention contemplates incorporation of at least one restriction enzyme site located on either side of each internal control DNA sequence to allow one or more of such internal control sequences to be released from said plasmid. The preferred embodiment of this feature further contemplates that having said multiple internal controls on one plasmid will allow substantial uniform quantitation of internal control DNA sequences relative to one another thereby making it possible to compare PCR quantitation results of cl versus test template amplification.

Other objects and advantages of the present invention will become apparent in the following description of the invention.

BRIEF DESCRIPTION OF THE DRAWINGS

FIG. 5 is a frequency array showing the expected ratios of test to control PCR products as detected by the hybridization methodology of the invention.

DETAILED DESCRIPTION OF THE INVENTION

Overview of Applications of the Methodology

Figure 1:
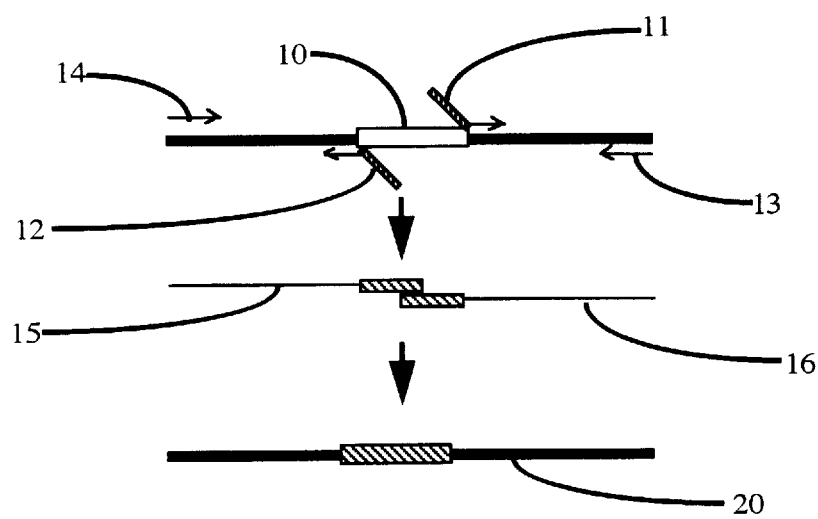
FIG. 1 depicts PCR-based construction strategies for the internal control template for quantitative PCR.

As stated generally above, one application of the current invention is detection of chromosome aneuploidy, including trisomy 21, 18, 13 and sex chromosome abnormalities. Such aneuploidies are gene dose abnormalities at the chromosome level.

Another application of the current invention relates to subchromosomal abnormalitites such as subchromosomal deletion mutations of which one example is loss of heterozygocity (LOH) in cancer cells, an abnormality which indicates that a normal copy of a tumor suppressor gene has been deleted. Another subchromosomal anomaly is the deletion of gene sequence that causes various syndromes called microdeletion syndromes. The current invention contemplates diagnosing such syndromes by selecting target sequences within affected gene regions (i.e. the deletion regions) and comparing the gene dose of such deletions versus internal controls. Examples of chromosome microdeletion syndromes include: Prader-Willi and Angelman's syndrome (deletion site 15q11–q13), William's syndrome (deletion site 7q11.23), Cri du chat syndrome (deletion site 5p), Langer-Giedion syndrome (deletion site 8q24.1), WAGR (deletioin site 11p13), Retinoblastoma (deletion site 13q14), Rubinstein-Taybi (deletion site 16p13.3), Smith-Magenis (deletion site 17p11.2), Miller-Dieker (deletion site 17p13.3), Alagille (deletion site 20p11.2–p12), DiGeorge's syndrome (deletion site 22q 11.2), Duchenne's/Becker's syndrome (deletion site Xp21), Congenital adrenal hypoplasia (deletion site Xp21), Chronic Granulomatous disease (deletion site Xp21), Steroid sulfatase deficiency (deletion site Xp22), and X-linked lymphorproliferative disease (deletion site Xq26).

Overview of Quantitative PCR Methodology

To achieve these and other objects, according to the present invention, DNA is extracted from fetal cells by standard DNA extraction techniques well known in the art, having first been obtained by procedures such as amniocentesis or chorionic villus sampling. The extracted DNA is then measured for concentration and after appropriate dilution, an aliquot is added to the PCR reaction tube. Next, PCR reaction components are added to the tube including appropriate concentrations of enzymes and buffers, biotinylated primers to chromosome loci desired to be examined, and control templates from an appropriate dilution of pre-digested control template plasmid wherein the control template sequence segments have been released from the plasmid in equal ratios to one another.

The PCR is allowed to proceed for an appropriate number of cycles after which the PCR product is denatured and added to microtiter wells for each chromosome to be examined. A preferred embodiment of the invention contemplates that the microtiter wells are coated with "capture" DNA oligomers having sequence complimentary to either the native chromosome sequence or the mutant sequence of the internal control. The preferred embodiment further contemplates that the PCR products are added to such micro titer wells under conditions which foster hybridization of the PCR products with the capture sequences.

Following hybridization, the microtiter wells are washed under appropriately stringent conditions and screened using colorimetric methodology to detect the level of captured PCR product.

Overview of Internal Control Mutant DNA
Sequence Design and Construction

The current invention provides for a significant advance over prior quantitative PCR technology by recognition of the effects which minor variations in DNA template size and nucleotide content have on amplification rates. Moreover, due to the ability to utilize same size templates for both test and control sequences, the current invention is not dependent upon seeking regions of the chromosome that may (or may not) have variability in length (e.g. STR regions).

Moreover, the current invention is not dependent upon methodology requiring reasonable separation of amplified species. Instead, the current invention is able to utilize chromosome regions of single copy per chromosome and is further able to use methodology capable of detection without prior separation of amplified species.

The preferred embodiment of the invention contemplates using PCR primers for amplifying test wildtype and control templates having identical primer binding sites. The preferred embodiment further contemplates the use of test and control templates of the same nucleotide length and G/C ratio content. A further preferred object of the invention contemplates the mutation of a short segment within the control template such that the mutation results in DNA sequence that has the same nucleotide content (in terms of bases A, G, C, and T present) and hybridization characteristics as the wildtype but differs in that the mutation is a radically different linear DNA sequence than the wildtype. In other words, the wildtype sequence in an internal section of the control template is scrambled either randomly or by specific design.

The preferred embodiment of such mutated sequence and its adjoining wildtype sequences external to the mutation contemplates that the control template retain the identical thermal dynamic properties of the wildtype test template. Moreover, the current invention does not intend to cover prior art such that it specifically excludes mutations in the internal control sequence that are intended to result in either the purposeful creation or destruction of restriction enzyme sites that might be designed for the purposes of separating the amplified internal controls from the wildtype test templates by electrophoretic methodology.

As illustrated in FIG. 1, the control template may be constructed by designing overlapping primer oligomers 11 and 12 having 5' DNA sequence that is a mutation of the wildtype target (i.e. test) sequence. Primers 11 and 12 have a 3' portion which is complementary to wildtype DNA. After initiating several cycles of PCR containing only primers 11 and 12 and a test template sequence 10, primers 13 and 14 containing 3' sequence that is complementary to wildtype sequence are added to the PCR reaction tube for the appropriate number of cycles to generate internal control sequence 20. Since both internal control sequence 20 and a wildtype segment of the same size as segment 20 will be generated in the PCR tube, the desired species 20 is isolated via hybridization techniques. Following separation, internal control sequence 20 may be amplified in pure form. Primers 13 and 14 may be designed to be complimentary to any portion of a chromosome (or other such genomic or cDNA) such that a PCR product generated may be of any length reasonably useful for detecting the amplified species by hybridization techniques. The 5' ends of primers 13 and 14 are designed so as to include at least one enzyme restriction site. The restriction site chosen must not exist within the test or internal control sequences. This restriction site will allow the control sequence 20 to be ligated into a plasmid with other control sequence templates.

Another method by which the internal control may be generated is to add primers 11 and 13 in one PCR tube and primer 12 and 14 in a separate tube such that species comprising one half of the internal control are generated in each reaction tube. The amplified species may then be isolated and mixed together in a fresh reaction with primers 13 and 14 to generate the desired full length species. Since the mutant primers 11 and 12 are designed to overlap (i.e. is complementary) at their 5' ends, the full length internal control species will be generated. This full length segment can then be isolated for cloning into the internal control containing plasmid.

In a preferred embodiment, DNA sequence marker for chromosome 21 specific sequence targets a 210 base pair sequence from its base number 371 to base number 580 within the human PCP4 gene (GenBank access No. U53709). SEQ ID NO 1 and SEQ ID NO 2 denote sequence specific for the 5' and 3' ends of this sequence respectively. The 5' ends of each of these sequences includes base sequence for an Eco RI restriction site. These sequences may be used as primers for gene-dose PCR analysis but preferably are used to generate chromosome 21 specific internal control sequence to be cloned into the internal control plasmid.

SEQ ID NO 1
5'GGG<u>AATTC</u>ACATGGATGCACCAGAGACAGAAC3'

SEQ ID NO 2
 Eco RI
5'GGG<u>AATTC</u>GCTATGCGTGTGTGGATTGTGTGT3'

The internal mutant sequence for chromosome 21 of the preferred embodiment using the PCP4 gene may be generated by sequences such as the sequences disclosed in SEQ ID NO 3 and NO 4.

SEQ ID NO 3 5'GAACCGTGACAGGCTACCCCCTCCTA3'

SEQ ID NO 4 5'CTGTCACGGTTCACAACCCAGCCTTC3'

Sequence No. 3 is a plus strand sequence having 16 bases of 5' mutant sequence of which the 5' most 12 bases complement, or overlap the 5' end of Seq. No. 4, while the 10 bases at the 3' end represent wildtype sequence. Likewise, Seq. No. 4 is a reverse strand sequence having 16 bases of 5' mutant sequence of which 12 bases compliment the 5' end of Seq. No. 3, while its 10 3' end bases represent wildtype sequence. Primer Seq. No. 1 and 4 may be used to generate the 5' half of the internal control sequence while Seq. Nos. 3 and 2 may be used to generate the 3' half of the internal control sequence. The full length chromosome 21 internal control sequence generated from these primers will have a mutant sequence 20 base pairs in length flanked on either side by 80 bases 5' and 110 bases 3' of wildtype sequence thereby resulting in an internal control sequence of the same length as the wildtype 210 base pair sequence plus additional base pairs of restriction site sequence.

In a preferred embodiment DNA sequence for chromosome 18 specific sequence targets 179 base pairs of the human myelin basic protein gene from its base number 562 to base number 740 within the myelin gene (GenBank access No: L18866). SEQ ID NO 5 and SEQ ID NO 6 denote sequence specific for the 5' and 3' ends of this gene sequence respectively. The 5' ends of each of these sequences includes base sequence for an Eco RI restriction site. These sequences may be used as primers for gene-dose PCR analysis but preferably are used to generate chromosome 18 specific internal control sequence to be cloned into the internal control plasmid.

SEQ ID NO 5 5'GGG<u>AATTC</u>CAAGAAGACAGTGCAGCCACCT3'
       Eco RI
 SEQ ID NO 6 5'GGG<u>AATTC</u>CCAAAGAAGCGCCCGATGGA3'

The internal mutant sequence for chromosome 18 of the preferred embodiment using the myelin gene may be generated by sequences such as the sequences disclosed in SEQ ID NO 7 and NO 8.

SEQ ID NO 7 5'AGCCACCGACAGGATATGCCAGGCAT3'

SEQ ID NO 8 5'CTGTCGGTGGCTGATTGGCCAGGTAC3'

Sequence No. 7 is a plus strand sequence having 16 bases of 5' mutant sequence of which the 5' most 12 bases complement, or overlap the 5' end of Seq. No. 8, while the 10 bases at the 3' end represent wildtype sequence. Likewise, Seq. 8 is a reverse strand sequence having 16 5' end bases of mutant sequence of which 12 bases compliment the 5' end of Seq. No. 7, while its 10 3' end bases represent wildtype sequence. Primer Seq. Nos. 5 and 8 may be used to generate the 5' half of the internal control sequence while Seq. Nos. 7 and 6 may be used to generate the 3' half of the internal control sequence. The full length chromosome 18 internal control sequence generated from these primers will have a mutant sequence 20 base pairs in length flanked on either side by 90 bases 5' and 69 bases 3' of wildtype sequence thereby resulting in an internal control sequence of the same length as the wildtype 179 base pair sequence plus additional base pairs of restriction site sequence.

In a preferred embodiment DNA sequence for chromosome 13 specific sequence targets 226 base pairs of the human endothelin-b receptor gene from its base number 1176 to base number 1401 within the endothelin-b receptor gene (GenBank access No: D13162). SEQ ID NO 9 and SEQ ID NO 10 denote sequence specific for the 5' and 3' ends of this gene sequence respectively. The 5' ends of each of these sequences includes base sequence for an Eco RI restriction site. These sequences may be used as primers for gene-dose PCR analysis but preferably are used to generate chromosome 13 specific internal control sequence to be cloned into the internal control plasmid.

SEQ ID NO 9 5'GGG<u>AATTC</u>GTGTCCTGTCTTCCTTCCTCTGC3'
       Eco RI
 SEQ ID NO 10 5'GGG<u>AATTC</u>GCGTCATTATCTCTGCGGTTTG3'

The internal mutant sequence for chromosome 13 of the preferred embodiment using the endothelin-b receptor gene may be generated by sequences such as the sequences disclosed in SEQ ID NO 11 and NO 12.

SEQ ID NO 11 5'GGCTCCGGTGCTGGTTTGCGGCCTGT3'

SEQ ID NO 12 5'AGCACCGGAGCCAAGAGGGCGCGTCC3'

Sequence No. 11 is a plus strand sequence having 16 bases of 5' mutant sequence of which the 5' most 12 bases complement, or overlap with the 5' end of Seq. No. 12, while the 10 bases at the 3' end represent wildtype sequence. Likewise, Seq. No. 12 is a reverse strand sequence having 16 5' end bases of mutant sequence of which 12 bases compliment the 5' end of Seq. No. 11 while its 10 3' end bases represent wildtype sequence. Primer Seq. Nos. 9 and 12 may be used to generate the 5' half of the internal control sequence while Seq. Nos. 11 and 10 may be used to generate the 3' half of the internal control sequence. The full length chromosome 13 internal control sequence generated from these primers will have a mutant sequence 20 base pairs in length flanked on either side by 118 bases 5' and 88 bases 3' of wildtype sequence thereby resulting in an internal control sequence of the same length as the wildtype 226 base pair sequence plus additional base pairs of restriction site sequence.

In a preferred embodiment DNA sequence for chromosome X specific sequence targets 160 base pairs of the human iduronate-2-sulphatase gene from its base number 2150 to base number 2309 within the iduronate-2-sulphatase gene (GenBank access No: L36845). SEQ ID NO 13 and SEQ ID NO 14 denote sequence specific for the 5'and 3' ends of this gene sequence respectively. The 5' ends of each of these sequences includes base sequence for an Eco RI restriction site. These sequences may be used as primers for gene-dose PCR analysis but preferably are used to generate chromosome X specific internal control sequence to be cloned into the internal control plasmid.

SEQ ID NO 13  5'GGG<u>AATTC</u>GCTCTAGGTGAACATGGAGAATGG3'
       Eco RI
SEQ ID NO 14  5'GG<u>GAATTC</u>TCAACTGTGAGGCGGAATCAAAAG3'

The internal mutant sequence for chromosome X of the preferred embodiment using the iduronate-2-sulphatase gene may be generated by sequences such as the sequences disclosed in SEQ ID NO 15 and NO 16.

SEQ ID NO 15 5'CAGGGTTGCACAGGTTGCTTCACTTC3'

SEQ ID NO 16 5'TGTGCAACCCTGGAATATATCAGGGG3'

Sequence No. 15 is a plus strand sequence having 16 bases of 5' mutant sequence of which the 5' most 12 bases complement, or overlap with the 5' end of Seq. No. 16, while the 10 bases at the 3' end represent wildtype sequence. Likewise, Seq. No. 16 is a reverse strand sequence having 16 5' end bases of mutant sequence of which 12 bases compliment the 5' end of Seq. No. 15 while its 10 3' end bases represent wildtype sequence. Primer Seq. Nos. 13 and 16 may be used to generate the 5' half of the internal control sequence while Seq. Nos. 15 and 14 may be used to generate the 3' half of the internal control sequence. The full length chromosome X internal control sequence generated from these primers will have a mutant sequence 20 base pairs in length flanked on either side by 70 bases 5' and 70 bases 3' of wildtype sequence thereby resulting in an internal control sequence of the same length as the wildtype 160 base pair sequence plus additional base pairs of restriction site sequence.

A further issue concerning the amplification of several target species simultaneously is the problem of preferential amplification due to, among other things, variability in primer G and C content, primer length, and primer hairpin and cross reaction with non-targeted species sequences. The current invention has provided for the avoidance of preferential amplification by designing primers to the different targeted sequences such that the primers are generally of the same length, G and C content, and hybridization melting temperatures.

Overview of Control Template Plasmid Construct

Figure 2:
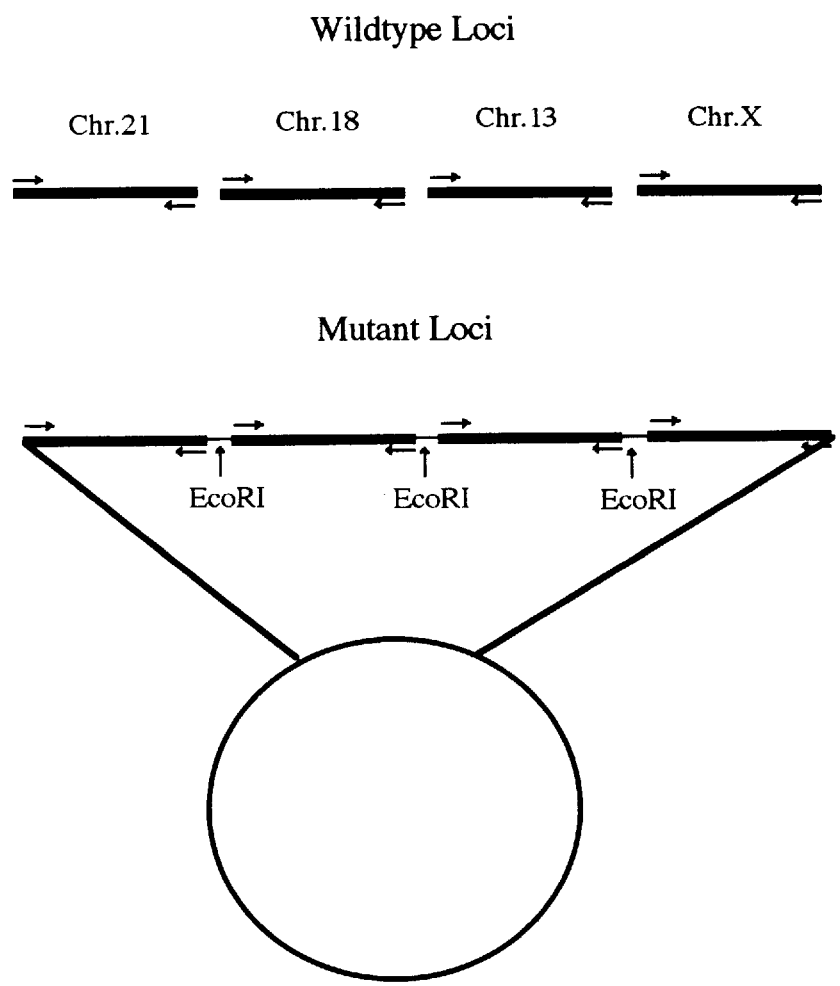
FIG. 2 shows a recombinant clone containing a tandem array of each chromosome specific internal control template.

The current invention contemplates use of any plasmid which can carry stable inserts of up to at least 4,000 base pairs. As shown in FIG. 2, a preferred embodiment of the current invention contemplates cloning internal control segments coding for various chromosomal markers into the Eco RI or other restriction site of plasmid puc 18 or other common plasmid vector. It is an object of the invention that the particular restriction sites chosen, either for the plasmid cloning site or the internal control cloning restriction sites, is not present within the test sequences and internal control's wildtype and mutant sequences. The internal control segments, after amplification in pure form are digested with the appropriate enzyme to make available their respective sticky or blunt ends, as the case may be, and then ligated into the aforementioned plasmid cloning site. The plasmid containing the desired internal control segments is then screened by restriction analysis to ensure that only one copy of each internal control segment is present. As indicated in FIG. 2, each internal control has sequence on its respective 5' and 3' ends complimentary to oligo primers specific for that chromosomal marker (indicated by arrows).

Overview of Capture Sequence Construction

In a preferred embodiment of the invention the 5' ends of capture oligonucleotides are synthesized using a primary amine allowing the oligomers to be covalently linked to specially treated microplates (Corning Costar Corp., Kennebunk Me.). The first ten nucleotides of the capture oligomers are designed to allow spacing between the plate surface and capture sequence. Generally, the specific sequences for capturing test and internal control PCR amplification products are designed to compliment the full mutant sequence length of the internal control or a corresponding region of the wildtype sequence on the test sequence PCR product. In a preferred embodiment of the current invention, the sequences for capturing will comprise enough nucleotides to allow hybridization under moderately stringent hybridization conditions. The current invention contemplates capture sequences of generally 10 to 100 nucleotides in length, usually 15 to 30 nucleotides in length and preferably 18 to 25 nucleotides in length.

For chromosome 21, the preferred capture probe for the test wildtype sequence targets at least one strand of the wildtype sequence PCR product comprising the twenty bases from base number 451 to base number 460 of the aforementioned 210 base pair sequence from human PCP4 gene. One such strand sequence is disclosed in SEQ ID NO 17. For the chromosome 21 capture sequence for the mutant region of the internal control, the preferred sequence is complementary to the twenty bases of mutant sequence such that the capture sequence spans the twenty bases of at least one strand of the mutant sequence PCR product (derived from SEQ ID NOs 3 and 4). One such mutant capture sequence is disclosed in SEQ ID NO 18.

SEQ ID NO 17  5'<u>AAATATTAAT</u> CTCAGTCCTAGTGGGAGAA3'
     anchor leader  capture specific sequence
SEQ ID NO 18  5'<u>AAATATTAAT</u> TGTGAACCGTGACAGGCTA3'

For chromosome 18, the preferred capture probe for the test wildtype sequence targets at least one strand of the wildtype sequence PCR product comprising the twenty bases from base number 652 to base number 671 of the aforementioned 179 base pair sequence from human myelin basic protein gene. One such strand sequence is disclosed in SEQ ID NO 19. For the chromosome 18 capture sequence for the mutant region of the internal control, the preferred sequence is complementary to the twenty bases of mutant sequence such that the capture sequence spans the twenty bases of at least one strand of the mutant sequence PCR product (derived from SEQ ID NOs 7 and 8). One such mutant capture sequence is disclosed in SEQ ID NO 20.

SEQ ID NO 19  5'<u>AAATATTAAA</u> CAGCAAGTACCATGGACCA3'
     anchor leader  capture specific sequence
SEQ ID NO 20  5'<u>AAATATTAAA</u> ATCAGCCACCGACAGGATA3'

For chromosome 13, the preferred capture probe for the test wildtype sequence targets at least one strand of the wildtype sequence PCR product comprising the twenty bases from base number 1294 to base number 1313 of the aforementioned 226 base pair sequence from human endothelin-b receptor gene. One such strand sequence is disclosed in SEQ ID NO 21. For the chromosome 13 capture sequence for the mutant region of the internal control, the preferred sequence is complementary to the twenty bases of mutant sequence such that the capture sequence spans the twenty bases of at least one strand of the mutant sequence PCR product (derived from SEQ ID NOs 11 and 12). One such mutant capture sequence is disclosed in SEQ ID NO 22.

SEQ ID NO 21  5'<u>AAATATTAAT</u> <u>GGTTGCGCTGGTTCTTGCC</u>3'
               anchor leader     capture specific sequence
SEQ ID NO 22  5'<u>AAATATTAAT</u> <u>CTTGGCTCCGGTGCTGGTT</u>3'

For chromosome X, the preferred capture probe for the test wildtype sequence targets at least one strand of the wildtype sequence PCR product comprising the twenty bases from base number 2220 to base number 2239 of the aforementioned 160 base pair sequence from human iduronate-2-sulphatase gene. One such strand sequence is disclosed in SEQ ID NO 23. For the chromosome X capture sequence for the mutant region of the internal control, the preferred sequence is complementary to the twenty bases of mutant sequence such that the capture sequence spans the twenty bases of at least one strand of the mutant sequence PCR product (derived from SEQ ID NOs 15 and 16). One such mutant capture sequence is disclosed in SEQ ID NO 24.

SEQ ID NO 23  5'<u>AAATATTAAT</u> <u>CTATGTTCCTGGAAGGACG</u>3'
               anchor leader     capture specific sequence
SEQ ID NO 24  5'<u>AAATATTAAA</u> <u>TTCCAGGGTTGCACAGGTT</u>3'

In a preferred embodiment, the capture oligomers are synthesized using a 5' terminal primary amine. The oligos are anchored to N-oxysuccinimide amine binding microtiter plates (Corning Costar Corp., Cambridge, Mass.). Each well contains a separate oligo for either a wildtype or an internal control sequence. The oligos are diluted so as to place from about 100 ng to 1 ug of DNA oligomer capture sequence into each well. Attachment of the oligos to each well is carried out by adding the DNA to the wells in the presence of PBS at pH 9, followed by incubation for 1 hour at room temperature (25° C.). The wells are then washed with 2 mM Imidizole buffered saline, 0.02% Tween 20. Unreacted attachment sites of the wells are blocked with Stabilcoat (BSI Corp., Eden Prairie, Minn.) for 30 minutes at room temperature followed by drying the wells of the attachment protocol solutions.

PCR Protocol and Detection Methodology

Figure 3:
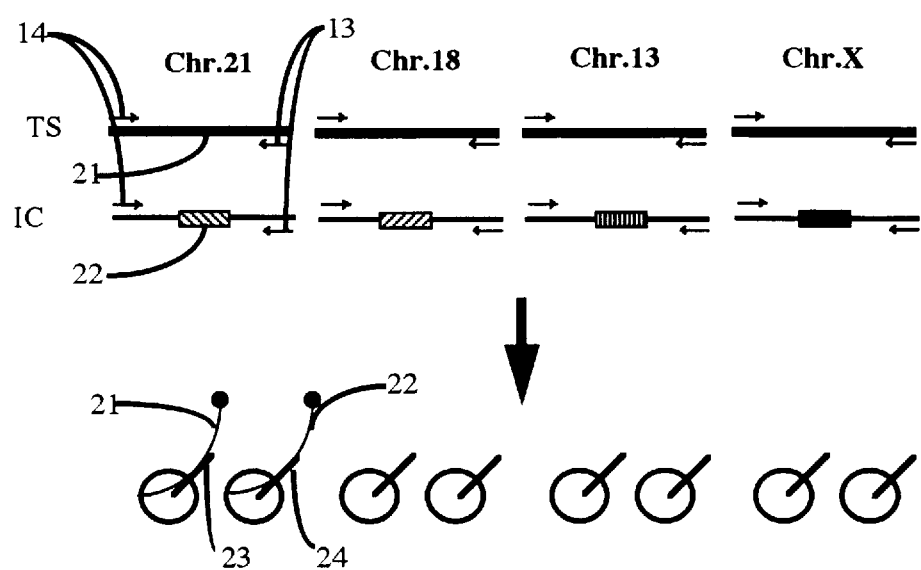
FIG. 3 shows a pictorial conception of the quantitative PCR hybridization detection protocol noting specific binding per well.
Figure 4:
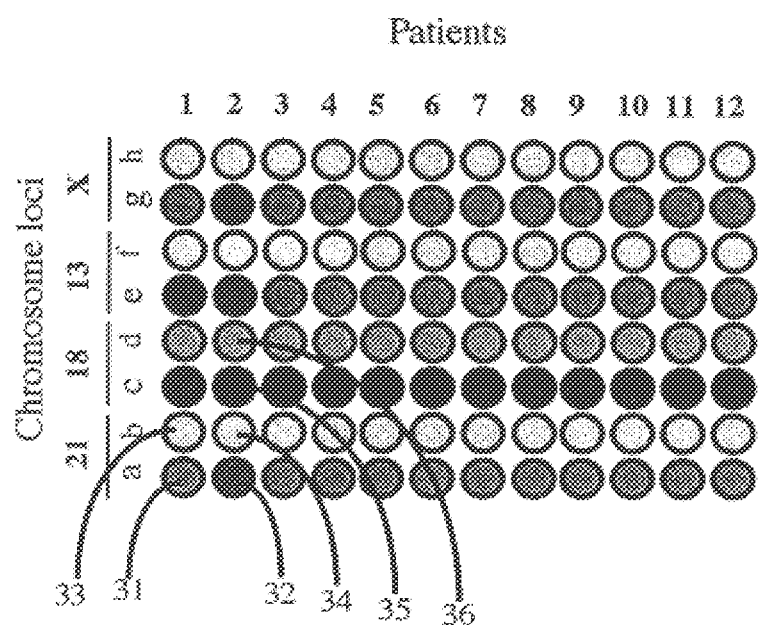
FIG. 4 depicts a typical array format for testing a multiplicity of patients to an array of chromosomal markers according to the invention.

As schematically indicated in FIGS. 3 and 4, PCR amplification products obtained for various chromosome markers and their corresponding internal controls, all of which have been amplified in a single reaction tube, are added to capture oligo containing microplate wells. In a preferred embodiment it is contemplated that the conditions for treating amplification products in the reaction mixture during hybridization will vary from environments appropriate for PCR amplification. Thus, following PCR amplification the reaction mixtures are diluted in hybridization solution the conditions of which will promote denaturation and reannealing of the PCR products either to their complimentary strands or to the capture probes.

As shown in FIG. 3, the array of chromosome markers are run in parallel. The detection process is delineated for chromosome 21. Primers 13 and 14 specific for the chromosome 21 anomaly detection are used to amplify both the wildtype test sequence (TS) 21 and the internal control (IC) 22. Following PCR, aliquots of the PCR are hybridized to capture sequences 23 and 24 which are in the microtiter wells. In the FIG. 3 example, capture sequence 23 is specific for wildtype sequence 21 and capture sequence 24 is specific for internal control 22.

FIG. 4 depicts a schematic of a microtiter plate and results typically expected for any given series of tests. Each patient may be tested for a series of chromosomal anomalies. FIG. 4 shows testing for chromosome anomalies of chromosome 21, 18, 13, and X. Each chromosome tested has two microtiter wells corresponding to either the wildtype capture well or the internal control capture well for that specific chromosome. Chromosome 21 has wildtype well "a" and internal control well "b". Each chromosome tested has two such wells also, one corresponding to wildtype and the other to mutant capture sequence. Refering to FIG. 5, in each of the ratio examples, letters in the denominator (b,d,f, h) denote internal controls while letters in the numerator (a,c,e, and g) denote wildtype.

Since testing in an array generates the simultaneous amplification of several genetic markers, the ratios between each amplified species may be compared to develop a profile for each test subject. FIG. 4 depicts the variability that will naturally exist between different test samples of a single patient as well as the variability that will exist between different patients. As suggested in FIG. 4, it is possible for two individuals to have different PCR yields at a particular locus due to differences in the concentration of wildtype templates (compare well 31 to well 32). It is also possible for an individual to have variable amplification rates from one chromosome locus to another (e.g. patient number 2 chromosome wildtype well 32 compared with chromosome 18 well 35, and comparison of internal control wells 34 and 36). Such variation within a single patient are due to differences in PCR target size and the fact that different primer sets may have different amplification efficiency. This variability in rates of amplification and efficiency is not material to the present invention as detection of any chromosomal anomaly is found by taking the ratio of the amplification found. For example, even though chromosome marker 18 may amplify more efficiently than chromosome 21, the ratio between the wildtype and internal control for chromosome 21 and that for chromosome 18 should remain constant if no chromosome anomaly exists, i.e. the ratio should be 1:1. Since the rate is comparable between chromosome loci, it is possible to calculate gene dosage.

As shown in FIG. 5, the gene dosage and related chromosome ratio for each chromosome of interest can be calculated. As is easily calculated by one of ordinary skill in the art, FIG. 5 shows the calculation of expected ratios for each of various chromosomal conditions. The wildtype is compared to its internal control value. The value resulting is then compared to like values of each of the other marker sequences tested (i.e. chromosome 21, 18, 13, X, or other genetic disorder). As shown in FIG. 5, normal female ratios are distinguishable from trisomies 13,18, and 21 in females. In another example, using the set of chromosome markers listed in FIG. 5 will not differentiate Kleinfelter's syndrome from normal female, but by adding a Y chromosome specific amplicon, including both wildtype and mutant controls, Kleinfelter's syndrome patients can be differentiated from normal females because the ratio of the Y mutant and wildtype may be compared.

At least one of each primer pair used to create the amplified sequences are labeled at the 5' end with biotin. The biotin will allow colorimetric analysis for detecting whether the target or internal control has been captured. Although the same primers that were used to construct the 5' and 3' ends of the internal controls could also be labeled with biotin and used for gene-dose PCR, the preferred embodiment contemplates using primers that have only wildtype sequence as opposed to foreign sequence such as restriction site sequence. The primary concern for preferably using only wildtype sequence is that the test sequence should contain only the exact G and C content and length of the internal control. Although both species may be amplified using a primer having extra linker/restriction site sequences, if such sequences are present, the initial annealing behavior of such a primer in the first few PCR cycles may vary enough between test sequence and internal control to cause inaccuracies to become manifest in the ratios ultimately realized between amplified species.

Examples of primers that could be used for chromosome 21 aneuploidy are shown in SEQ ID NOs 25 and 26 directed to the 5' and 3' ends, respectively, of the aforementioned 210 base pairs of the human PCP4 gene.

SEQ ID NO 25 5'ACATGGATGCACCAGAGACAGAAC3'

SEQ ID NO 26 5'GCTATGCGTGTGTGGATTGTGTGT3'

Examples of primers that could be used to detect chromosome 18 are shown in SEQ ID NOs 27 and 28 directed to the 5' and 3' ends, respectively, of the aforementioned 179 base pairs of the human myelin basic protein gene.

SEQ ID NO 27 5'CAAGAAGACAGTGCAGCCACCT3'

SEQ ID NO 28 5'CCAAAGAAGCGCCCGATGGA3'

Examples of primers that could be used to detect chromosome 13 are shown in SEQ ID NOs 29 and 30 directed to the 5' and 3' ends, respectively, of the aforementioned 226 base pairs of the human endothelin-b receptor gene.
SEQ ID NO 29 5'GTGTCCTGTCTTCCTTCCTCTGC3'

SEQ ID NO 30 5'GCGTCATTATCTCTGCGGTTTG3'

Examples of primers that could be used to detect chromosome X are shown in SEQ ID NOs 31 and 32 directed to the 5' and 3' ends, respectively, of the aforementioned 160 base pairs of the human iduronate-2-sulphatase gene.

SEQ ID NO 31 5'GCTCTAGGTGAACATGGAGAATGG3'

SEQ ID NO 32 5'TCAACTGTGAGGCGGAATCAAAAG3'

In a preferred embodiment, PCR amplification reaction mixtures utilize Perkin Elmer model number 480 thermocycler. The denaturing cycle is 1 minute at 94° C. The amplification cycles are allowed to proceed at 61 degrees for 45 seconds for annealing and 72 degrees and 45 seconds for extension.

After amplification, the PCR mixture is diluted and aliquots are dispensed into microwells for each chromosome or genetic marker to be tested. An aliquot of the PCR amplification will be added to the well containing test capture oligomers and to the well containing internal control capture oligomers for each tested anomaly. The preferred hybridization conditions contemplate methodology well known in the art.

Specifically, in one example, following amplification the PCR product is diluted in 25 ul of PBS, pH 7.25 then mixed with 25 ul of denaturing solution (0.8N Na OH) and then added to the probe containing microtiter wells and allowed to incubate for 10 minutes at room temperature. Next, 25 ul of 4X hybridization solution (pH 7.25, PBS, 8% BSA) and 25 ul of neutralizing solution (4M ammonium acetate) is added to the microtiter wells and allowed to incubate 5 minutes at room temperature, followed by incubation at 55° C. for 45 minutes. Next, the microtiter wells are washed with 1M tris-buffered saline pH 7.5 and 1% Tween 20 at room temperature.

After hybridization, colorimetric detection may be carried out by addition of streptavidin-horseradish peroxidase conjugate which specifically recognizes and binds to the biotin label in the captured PCR products. Presence of the bound conjugate may be determined after addition of o-phenylenediamine solution by measuring absorbance of each well spectrophotometrically at 492 nm. The procedure for such analysis is well documented in the art such as that methodology found in U.S. Pat. No. 5,612,473 herein incorporated by reference. Gene-dosage is determined by scanning the microplate after color development. In a similar method, the hybridized products of the PCR may also be detectable as bound species to the capture probes by adding 100 ul of streptavidin-alkaline phosphatase conjugate (SPA, Milan, Italy) for 30 minutes at 37° C. After incubation of the conjugate, the wells are washed with wash buffer ( 1M tris-buffered saline pH 7.5, 1% Tween 20), followed by incubation at 37° C. for 30 minutes in 100 ul of p-NPP solution (1 mg/ml p-nitrophenyl phosphate in 0.5M Tris, ph 9.5). The color reaction is terminated by adding 1.5N NaOH and absorbance values are determined using a 492 nm light source.

Overview of Experimental Data

EXAMPLE 1

Figure 6:
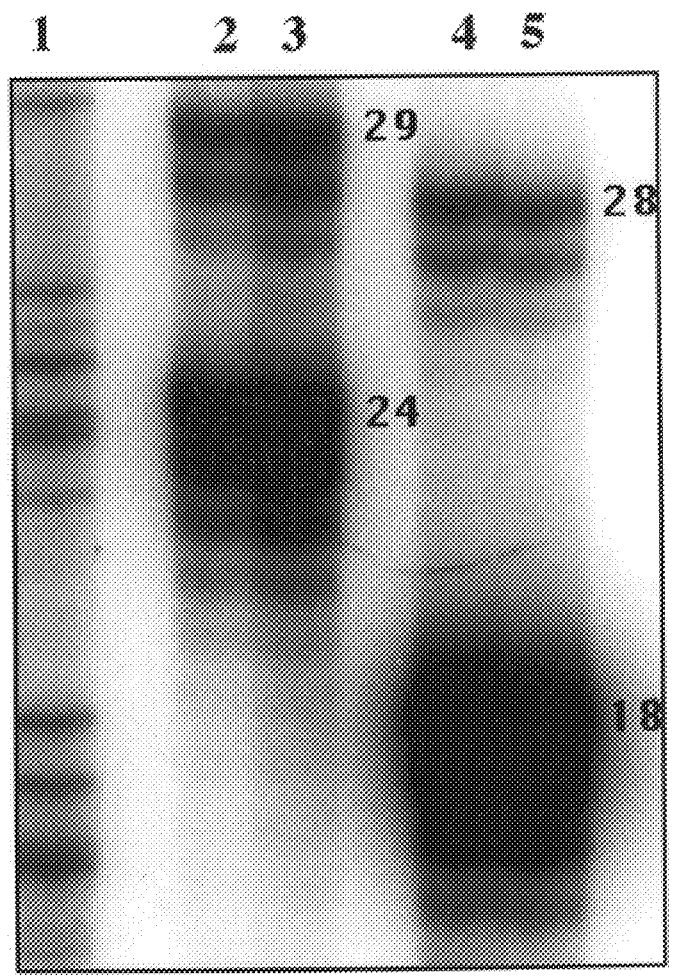
FIG. 6 shows a PAGE of PCR products obtained for STRs using protocols similar to prior art methods.

FIG. 6 shows typical results obtained from prior art methodologies wherein detection of aneuploidy is based on determining size of PCR products and/or quantitation of different sized PCR products. In the figure, the samples are double loaded in the lanes for clarity such that lanes 2 and 3 are identical and lanes 4 and 5 are identical. Lane 1 is a molecular weight marker indicating the size of PCR products. Lanes 2 through 5 show PCR products of an amplified region of the fragile X mental retardation gene locus. The primers used for each reaction were identical and were designed according to sequence in GenBank (Accession number X61378) such that they flanked a polymorphic CGG repeat that is expanded in patients expressing Fragile X syndrome. Normal individuals exhibit from 6 to 54 repeats and have further ranged in size to more than 200 repeats. In contrast Fragile X patients exhibit more than 230 repeats. Lanes 2 and 3 show results from a normal patient with allelic bands of 24 and 29 CGG repeats. Lanes 4 and 5 show PCR amplifications wherein another normal patient shows allelic bands having 18 and 28 repeats. This experiment demonstrates that even though the same PCR primers were used, there is measurable difference in the amplification of different sized targets notwithstanding the fact that the four alleles (with 29, 28, 24, and 18 repeats respectively) were amplified under the same PCR conditions and using the same primers. This example demonstrates the need for internal controls where quantitative PCR analysis is contemplated. Such quantitative PCR cannot yield useful data where amplified products of different sizes should be 1:1 ratios but result in vastly different ratios because the smaller PCR products are preferentially amplified. As can be observed in FIG. 6, there is added danger if observation of additional bands is necessary because the over amplified smaller bands may mask the presence of such additional bands.

The PCR reaction of FIG. 6 was designed following Levinson G. et al., American Journal of Medical Genetics. 51(4): 527–34, 1994. The PCR mixture contained 100 ng of genomic DNA, 200 um dNTP (75% deaza dGTP, 25% regular dGTP), 3 pmol of each primer, 0.75 ul alpha $^{32}$ P dCTP (3000Ci/mmol), PCR buffer, water, and Taq polymerase. The reaction was allowed to amplify 25 cycles wherein denature cycle was 95° C. at 90 seconds, annealing cycle 65° C. at 60 seconds, and amplification cycle 72° C. for 120 seconds with a final extension at 72° C. for 7 min. The PCR products were run on a 5% denaturing polyacrylamide gel and exposed to X-ray film.

EXAMPLE 2

FIG. 7 shows results typical of the current invention. This example presents the quantitative results in dot blot form as the accuracy of the present invention is more easily understandable. The dot blots represent conditions that would exist in a microtiter well of a microtiter plate. On each dot, 1 ug of capture oligomer (18W and 21W=chromosome 18 and 21 wildtype respectively, 18M and 21M=chromosome 18 and 21 internal control mutant sequences respectively,) was annealed to nylon paper. The 1 ug amount was chosen so that the capture sequences specific for the amplified PCR products would not reach saturation when hybridized to PCR product.

Figure 7A:
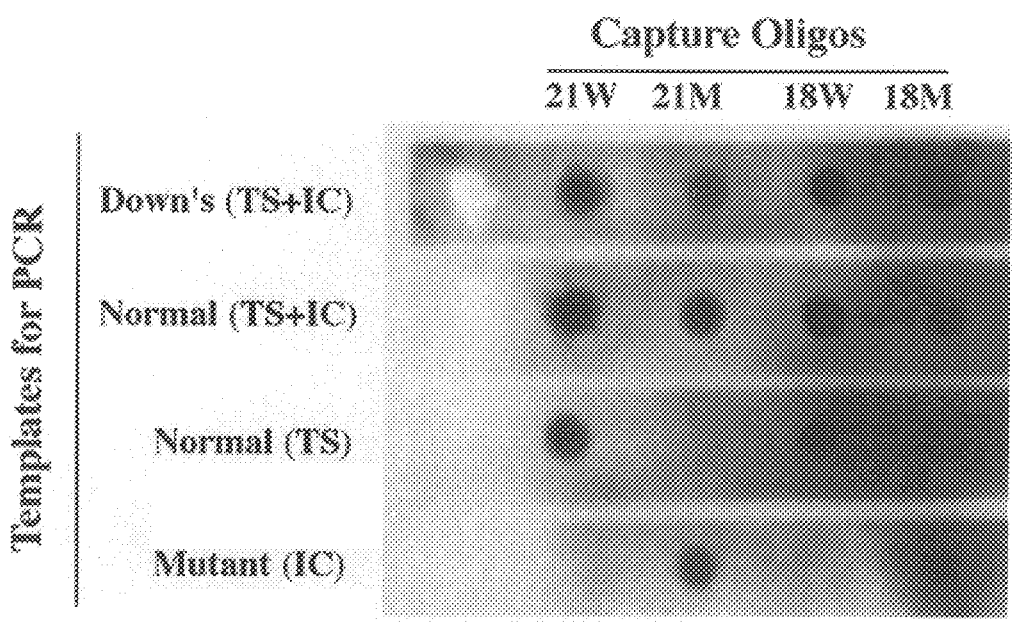
FIG. 7 shows a dot bot test using PCR reaction conditions of the current invention.
FIGS. 7b and 7c show numerical results of the dot blot test of FIG. 7a using PCR reaction conditions of the current invention.
Figures 7B, 7C:
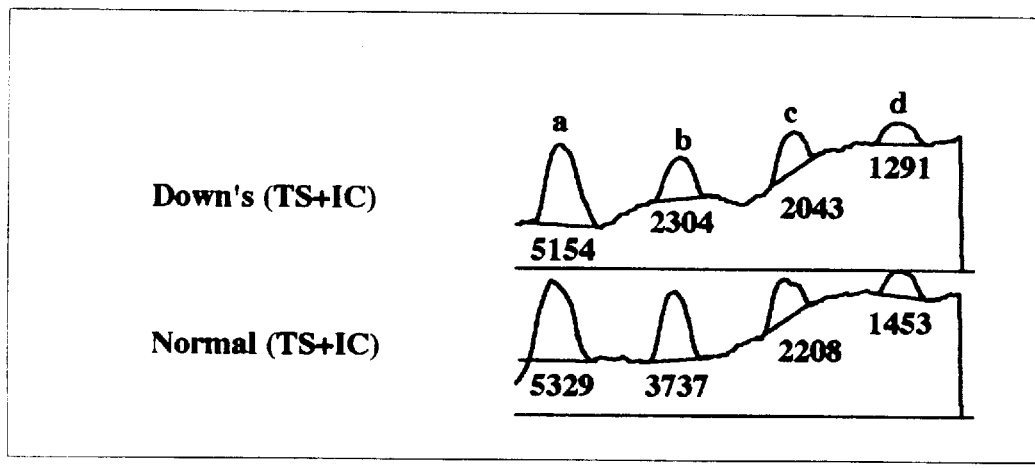

The PCR amplifications depicted in FIGS. 7a, 7b and 7c were carried out using 1 fg of mutant plasmid template and 100 ng of genomic DNA from test patients. Four PCRs were carried out to generate amplified products containing (1) Down's patient wildtype and internal control, (2) normal individual wildtype and internal control, (3) normal wildtype, and (4) internal control. The normal alone wildtype (3) and internal control alone (4) were prepared for the purpose of showing that the capture probes are specific to each of the chromosome 18 and 21 wildtype and their respective internal controls.

As shown in FIGS. 7a, 7b and 7c the Down's patient and normal individual wildtype and internal control blots were analyzed for density. Ratios were calculated per the embodiments of the invention such that the Down's patient ratios of the chromosome 18 and 21 yielded a ratio near the expected 1.5, and the normal patient ratio yielded a value near the expected 1.0.

Conditions for PCR used in mixtures to generate reactions for the Down's, normal patient, normal, and internal control include 200 uM dNTPs, 50 ng each of the four wildtype primers specific for chromosome 21 and 18, (SEQ ID Nos. 25 through 28) of which primers SEQ ID Nos. 26, and 28 were biotin labeled, 1 fg internal control template (EcoRI digested internal control plasmid wherein mutant templates for chromosome 18 and 21 had the same copy number), water, reaction buffer, and Taq polymerase.

Hybridization was carried out in buffer containing 40% deionized formamide, 2 mM EDTA, 0.9M NaCl, 32 mM NaH2PO4, 18 mM Na2HPO4, 0.1% Ficoll 400, 0.1% Polyvinylpyrrolidone, 5% Dextran Sulfate, and 1% SDS. The PCR mixture was heat denatured in hybridization buffer and hybridization was allowed to proceed 3 hours at 42° C. The blots were washed twice at room temperature with 1×SSC, 1% SDS for 5 minutes each followed by two washes in 0.5×SSC, 0.1% SDS at 42° C.for 5 minutes. Nonradioactive detection was carried out with a kit from Schleicher & Schuell (Cat #78030). Intensity of the dots, reflecting PCR yields were analyzed with NIH Image software. PCR yield was determined by measuring the intensity of each dot (as represented by the areas below the dots). Down's patient was identified to have an inter-loci wildtype/mutant ratio of about 1.5 (1.41), while the normal individual exhibited a ratio of about 1 (0.94).

Similar to ratios for trisomies, ratios for microdeletions are easily determined. Whereas trisomies result in increased ratios (derived from increased DNA content), microdeletions result in test samples having less DNA for PCR amplification. Thus, ratios between wildtype and mutant sequence for any specific locus will be decreased from a normal of 1:1 to 1:0.5.

BRIEF DESCRIPTION OF THE SEQUENCE LISTING

SEQ ID NO 1 and SEQ ID NO 2 are Eco RI containing primers for amplifying a 210 base pair segment of the human PCP4 gene.

SEQ ID NO 3 and SEQ ID NO 4 are primers that anneal to internal sections of the 210 base pair segment of the PCP4 gene and further include mutant sequence.

SEQ ID NO 5 and SEQ ID NO 6 are Eco RI containing primers for amplifying a 179 base pair segment of the human myelin basic protein gene.

SEQ ID NO 7 and SEQ ID NO 8 are primers that anneal to internal sections of the 179 base pair segment of the myelin gene and further include mutant sequence.

SEQ ID NO 9 and SEQ ID NO 10 are Eco RI containing primers for amplifying a 226 base pair segment of the human endothelin-b receptor gene.

SEQ ID NO 11 and SEQ ID NO 12 are primers that anneal to internal sections of the 226 base pair segment of the endothelin-b receptor gene and further include mutant sequence.

SEQ ID NO 13 and SEQ ID NO 14 are Eco RI containing primers for amplifying a 160 base pair segment of the human iduronate-2-sulphatase gene.

SEQ ID NO 15 and SEQ ID NO 16 are primers that anneal to internal sections of the 160 base pair segment of the iduronate-2-sulphatase gene and further include mutant sequence.

SEQ ID NO 17 through SEQ ID NO 24 are capture oligomers having a 5' end designed to attach to microwell plates and a 3' region capable of hybridizing to either wildtype or mutant sequence for each of the PCP4 gene (SEQ ID NOs 17 and 18), the myelin gene (SEQ ID NOs 19 and 20), the endothelin-b gene (SEQ ID NOs 21 and 22), and the iduronate-2-sulphatase gene (SEQ ID NOs 23 and 24).

SEQ ID NO 25 and SEQ ID 26 are wildtype primers for the PCP4 gene.

SEQ ID NO 27 and SEQ ID 28 are wildtype primers for the myelin gene.

SEQ ID NO 29 and SEQ ID 30 are wildtype primers for the endothelin-b gene.

SEQ ID NO 31 and SEQ ID 32 are wildtype primers for the iduronate-2-sulphatase gene.

Modifications and other embodiments of the invention will be apparent to those skilled in the art to which this invention relates having the benefit of the foregoing teachings, descriptions, and associated drawings. The present invention is therefore not to be limited to the specific embodiments disclosed but is to include modifications and other embodiments which are within the scope of the appended claims. All references are herein incorporated by reference.

I claim:

1. A kit to detect gene dosage having components comprising:

a) at least one pair of DNA oligonucleotides wherein one of said pair of DNA oligonucleotides is complimentary to a 5' nucleotide sequence of a targeted segment of genomic DNA sequence and the other oligonucleotide of said pair of DNA oligonucleotides is complimentary to a 3' nucleotide sequence of said targeted segment of genomic DNA sequence, at least one of said pair of DNA oligonucleotides further having a colormetric sensitive moiety covalently linked to a 5' nucleotide, said pair of DNA oligonucleotides further being capable of acting as primers in a polymerase chain reaction for amplifying the targeted segment of genomic DNA sequence;

b) DNA segments comprising internal control DNA sequences complimentary to the length of said targeted segment of genomic DNA sequences except for a central portion of said internal control DNA sequences which comprise non-natural synthetic DNA sequence, said non-natural synthetic DNA sequence representing a mutation of a corresponding same length portion of said targeted segment in said internal control DNA, said internal control DNA sequences further having a total base length and nucleotide base content equivalent to said targeted genomic DNA sequence, such internal control DNA segment length defined by annealing positions onto said internal control DNA of said DNA oligonucleotides of (a);

c) microwell plates having connected in each well of said plates at least one DNA oligonucleotide the sequence of which comprises a spacer DNA sequence and a DNA sequence complimentary to DNAs selected from the group consisting of (1) genomic DNA sequence, (2) a stable chromosome gene, (3) a single copy gene on a chromosome, (4) a non-natural mutant DNA sequence, and (5) a mammalian gene; and d) buffers and enzymes for carrying out (1) a polymerase chain reaction, (2) DNA—DNA hybridization and washing, and (3) colormetric quantatation.

2. A kit according to claim 1 wherein the targeted segments of genomic DNA sequence are selected from the group consisting of (1) human PCP4, (2) human myelin basic protein gene, (3) human endothelin-b receptor gene, and (4) human iduronate-2-sulphatase gene.

3. A kit according to claim 1 wherein the targeted segments of genomic DNA sequence are associated with microdeletions of chromosomal DNA selected from the group consisting of (1) deletion site 15q11-q13 of Prader-Willi and Angelman's syndrome, (2) deletion site 7q11.23 of William's syndrome, (3) deletion site 5p of Cri du chat syndrome, (4) deletion site 8q24.1 of Langer-Giedion syndrome, (5) deletioin site 11p13 of WAGR, (6) deletion site 13q14 of Retinoblastoma, (7) deletion site 16p13.3 of Rubinstein-Taybi, (8) deletion site 17p11.2 of Smith-Magenis, (9) deletion site 17p13.3 of Miller-Dieker, (10) deletion site 20p11.2-p12 of Alagille, (11) deletion site 22q11.2 of DiGeorge's syndrome, (12) deletion site Xp21of Duchenne's/Becker's syndrome, (13) deletion site Xp21 of Congenital adrenal hypoplasia, (14) deletion site Xp21 of Chronic Granulomatous disease, (15) deletion site Xp22 of Steroid sulfatase deficiency, and (16) deletion site Xq26 of X-linked lymphorproliferative disease.

4. A kit according to claim 1 for determining gene dosage for the purpose of detecting chromosome anomalies selected from the group consisting of (1) trisomy 13, (2) trisomy 18, (3) trisomy 21, and (4) X-chromosome anomalies.

5. DNA segments comprising internal control sequences according to claim 1 wherein a multiplicity of said DNA segments exist on a single plasmid, said plasmid having a single copy of each of said internal control segments.

6. DNA segments comprising internal control sequences of claim 1 having a total base pair length of between 55 and 2000 nucleotides.

7. Non-natural synthetic DNA sequences of claim 1 having a total DNA sequence length of between 10 and 100 bases.

8. Targeted segment of genomic DNA of claim 1 having a total targeted DNA segment length of about 55 to 2000 nucleotides.

9. A kit to detect gene dosage having components comprising:

a) at least one pair of DNA oligonucleotides wherein one of said pair of DNA oligonucleotides is complimentary to a 5' nucleotide sequence of a targeted segment of mammalian genomic DNA sequence and the other oligonucleotide of said pair of DNA oligonucleotides is homologous to a 3' nucleotide sequence of said targeted segment of mammalian genomic DNA sequence, at least one of said pair of DNA oligonucleotides further having a colormetric sensitive moiety covalently linked to a 5' nucleotide, said pair of DNA oligonucleotides further being capable of acting as primers in a polymerase chain reaction for amplifying the targeted segment of mammalian genomic DNA sequence;

b) DNA segments comprising internal control DNA sequences complimentary to the length of said targeted segment of mammalian genomic DNA sequences except for a central portion of said internal control DNA sequences which comprise non-natural synthetic DNA sequence, said non-natural synthetic DNA sequence representing a mutation of a corresponding same length portion of said targeted segment in said internal control DNA, said internal control DNA sequences further having a total base length and nucleotide base content equivalent to said targeted mammalian genomic DNA sequence, such internal control DNA segment length defined by annealing positions onto said internal control DNA of said DNA oligonucleotides of (a);

c) microwell plates having connected in each well of said plates at least one DNA oligonucleotide the sequence of which comprises a spacer DNA sequence and a DNA sequence complimentary to DNAs selected from the group consisting of (1) genomic DNA sequence, (2) a stable chromosome gene, (3) a single copy gene on a chromosome, (4) a non-natural mutant DNA sequence, and (5) a mammalian gene; and d) buffers and enzymes for carrying out (1) a polymerase chain reaction, (2) DNA—DNA hybridization and washing, and (3) colormetric quantatation.

10. A kit according to claim 9 wherein the targeted segments of mammalian genomic DNA sequence are selected from the group consisting of (1) human PCP4, (2) human myelin basic protein gene, (3) human endothelin-b receptor gene, and (4) human iduronate-2-sulphatase gene.

11. A kit according to claim 9 wherein the targeted segments of mammalian genomic DNA sequence are associated with microdeletions of chromosomal DNA selected from the group consisting of (1) deletion site 15q11-q13 of Prader-Willi and Angelman's syndrome, (2) deletion site 7q11.23 of William's syndrome, (3) deletion site 5p of Cri du chat syndrome, (4) deletion site 8q24.1 of Langer-Giedion syndrome, (5) deletioin site 11p13 of WAGR, (6) deletion site 13q14 of Retinoblastoma, (7) deletion site 16p 13.3 of Rubinstein-Taybi, (8) deletion site 17p 11.2 of Smith-Magenis, (9) deletion site 17p13.3 of Miller-Dieker, (10) deletion site 20p11.2-p12 of Alagille, (11) deletion site 22q11.2 of DiGeorge's syndrome, (12) deletion site Xp21of Duchenne's/Becker's syndrome, (13) deletion site Xp21 of Congenital adrenal hypoplasia, (14) deletion site Xp21 of Chronic Granulomatous disease, (15) deletion site Xp22 of Steroid sulfatase deficiency, and (16) deletion site Xq26 of X-linked lymphorproliferative disease.

12. A kit according to claim 9 for determining gene dosage for purposes of detecting chromosome anomalies selected from the group consisting of (1) trisomy 13, (2) trisomy 18, (3) trisomy 21, and (4) X-chromosome anomalies.

13. DNA segments comprising internal control sequences according to claim 9 wherein a multiplicity of said DNA segments exist on a single plasmid, said plasmid having a single copy of each of said internal control segments.

14. DNA segments comprising internal control sequences of claim 9 having a total base pair length of between 55 and 2000 nucleotides.

15. Non-natural synthetic DNA sequences of claim 9 having a total DNA sequence length of between 10 and 100 bases.

16. Targeted segment of mammalian genomic DNA of claim 9 having a total targeted DNA segment length of about 55 to 2000 nucleotides.

17. A method for detecting gene dosage differences comprising:

a) making a PCR reaction mixture by mixing components for a PCR in a single tube, said components comprising (1) genomic DNA, (2) at least one pair of DNA primer oligonucleotides wherein one of said pair is complimentary to a 5' sequence and the other of said pair is complimentary to a 3' sequence of a section of said genomic DNA, said length of said section of genomic DNA having between 55 and 2000 nucleotides, (3) internal control DNAs, said internal control DNAs having DNA sequence that is complimentary to said genomic DNA, said internal control DNAs further having non-natural synthetic DNA sequence, said internal control DNAs further having an overall nucleotide base length and nucleotide content equivalent to said section of said genomic DNA as such section of genomic DNA is defined at its 5' and 3' termini by any of said pair of DNA primer oligonucleotides, and (4) PCR buffers and enzymes necessary to carry out a polymerase chain reaction;

b) conducting a PCR of (a) for between 2 and 30 temperature cycles to create amplified PCR products;

c) dispensing portions of said PCR of b) into microwells which have been coated with at least one DNA oligonucleotide having a nucleotide sequence complementary to a nucleotide sequence selected from the group consisting of (1) a section of said genomic DNA, and (2) a non-natural synthetic DNA;

d) hybridizing said DNA oligonucleotide of said microwells with amplified PCR products of said PCR of (b); and e) detecting the presence and relative quantity of the amplified products.

18. Internal control DNAs according to claim 17 wherein a multiplicity of said internal control DNAs exist on a single plasmid, said plasmid having a single copy of each of said internal control DNAs.

19. A method according to claim 17 wherein the method is directed to detecting gene dosage differences to chromosome anomalies selected from the group consisting of (1) trisomy 13, (2) trisomy 18, (3) trisomy 21, and (4) X-chromosome anomalies.

20. A method according to claim 17 wherein the method is directed to detecting gene dosage differences to chromosome microdeletion anomalies selected from the group consisting of (1) deletion site 15q11-q13 of Prader-Willi and Angelman's syndrome, (2) deletion site 7q 11.23 of William's syndrome, (3) deletion site 5p of Cri du chat syndrome, (4) deletion site 8q24.1 of Langer-Giedion syndrome, (5) deletioin site 11p 13 of WAGR, (6) deletion site 13q14 of Retinoblastoma, (7) deletion site 16p13.3 of Rubinstein-Taybi, (8) deletion site 17p11.2 of Smith-Magenis, (9) deletion site 17p13.3 of Miller-Dieker, (10) deletion site 20p11.2-p12 of Alagille, (11) deletion site 22q11.2 of DiGeorge's syndrome, (12) deletion site Xp21 of Duchenne's/Becker's syndrome, (13) deletion site Xp21 of Congenital adrenal hypoplasia, (14) deletion site Xp21 of Chronic Granulomatous disease, (15) deletion site Xp22 of Steroid sulfatase deficiency, and (16) deletion site Xq26 of X-linked lymphorproliferative disease.

21. A method for detecting gene dosage differences comprising:

a) making a PCR reaction mixture by mixing components for a PCR in a single tube, said components comprising (1) DNA selected from the group consisting of procaryotic DNA and eukaryotic DNA, (2) at least one pair of DNA primer oligonucleotides wherein one of said pair is complimentary to a 5' sequence and the other of said pair is complimentary to a 3' sequence of a section of said procayotic or eukaryotic DNA, said length of said section of procaryotic or eukaryotic DNA having between 55 and 2000 nucleotides, (3) internal control DNAs, said internal control DNAs having DNA sequence that is complimentary to said procaryotic or eukarotic DNA, said internal control DNAs further having non-natural synthetic DNA sequence, said internal control DNAs further having an overall nucleotide base length and nucleotide content equivalent to said section of said procaryotic or eukaryotic DNA as such section of procaryotic or eukaryotic DNA is defined at its 5' and 3' termini by any of said pair of DNA primer oligonucleotides, and (4) PCR buffers and enzymes necessary to carry out a polymerase chain reaction;

b) conducting a PCR of (a) for between 2 and 30 temperature cycles to create amplified PCR products;

c) dispensing portions of said PCR of b) into microwells which have been coated with at least one DNA oligonucleotide having a nucleotide sequence complementary to a nucleotide sequence selected from the group consisting of (1) a section of said procaryotic or eukaryotic DNA, and (2) a non-natural synthetic DNA;

d) hybridizing said DNA oligonucleotide of said microwells with amplified PCR products of said PCR of (b); and e) detecting the presence and relative quantity of the amplified products by colormetric means.

22. Internal control DNAs according to claim 21 wherein a multiplicity of said internal control DNAs exist on a single plasmid, said plasmid having a single copy of each of said internal control DNAs.

23. A method according to claim 21 wherein the method is directed to detecting gene dosage differences to chromosome anomalies selected from the group consisting of (1) trisomy 13, (2) trisomy 18, (3) trisomy 21, and (4) X-chromosome anomalies.

24. A method according to claim 21 wherein the method is directed to detecting gene dosage differences to chromosome microdeletion anomalies selected from the group consisting of (1) deletion site 15q11-q13 of Prader-Willi and Angelman's syndrome, (2) deletion site 7q11.23 of William's syndrome, (3) deletion site 5p of Cri du chat syndrome, (4) deletion site 8q24.1 of Langer-Giedion syndrome, (5) deletioin site 11p13 of WAGR, (6) deletion site 13q14 of Retinoblastoma, (7) deletion site 16p 13.3 of Rubinstein-Taybi, (8) deletion site 17p11.2 of Smith-Magenis, (9) deletion site 17p13.3 of Miller-Dieker, (10) deletion site 20p11.2-p12 of Alagille, (11) deletion site 22q11.2 of DiGeorge's syndrome, (12) deletion site Xp21 of Duchenne's/Becker's syndrome, (13) deletion site Xp21 of Congenital adrenal hypoplasia, (14) deletion site Xp21 of Chronic Granulomatous disease, (15) deletion site Xp22 of Steroid sulfatase deficiency, and (16) deletion site Xq26 of X-linked lymphorproliferative disease.

* * * * *